US006228845B1

(12) United States Patent
Donovan et al.

(10) Patent No.: US 6,228,845 B1
(45) Date of Patent: May 8, 2001

(54) THERAPEUTIC INTRALUMINAL STENTS

(75) Inventors: Maura G. Donovan, St. Paul; Paul M. Stein, Maple Grove, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/176,519

(22) Filed: Oct. 21, 1998

Related U.S. Application Data

(62) Division of application No. 08/746,404, filed on Nov. 8, 1996, now Pat. No. 5,833,651.

(51) Int. Cl.$^7$ .......................... A61M 31/00; B29C 35/08; B29C 43/18
(52) U.S. Cl. .............................. 514/44; 604/53; 604/265; 604/1; 264/485; 264/279; 264/314
(58) Field of Search ......................... 604/53, 265; 623/1; 514/44; 264/485, 279, 314

(56) References Cited

U.S. PATENT DOCUMENTS

| 5,092,841 | 3/1992 | Spears ..................................... 604/96 |
| 5,199,951 | 4/1993 | Spears ..................................... 623/1 |
| 5,304,121 | 4/1994 | Sahatijan ................................ 604/53 |
| 5,334,201 | 8/1994 | Cowan ..................................... 623/1 |
| 5,449,382 | 9/1995 | Dayton ..................................... 623/1 |
| 5,498,238 | 3/1996 | Shapland et al. ....................... 604/53 |
| 5,500,013 | 3/1996 | Buscemi et al. ........................ 623/1 |
| 5,591,224 | 1/1997 | Schwartz et al. ....................... 623/1 |
| 5,591,227 | 1/1997 | Dinh et al. .............................. 623/1 |
| 5,599,307 | 2/1997 | Bacher et al. ......................... 604/101 |

FOREIGN PATENT DOCUMENTS

| 0 366 564 A2 | 5/1990 | (EP) . |
| 0 701 801 | 3/1996 | (EP) . |
| 0 701 802 | 3/1996 | (EP) . |
| WO 90/13332 | 11/1990 | (WO) . |
| WO 91/12779 | 9/1991 | (WO) . |
| WO 92/07573 | 5/1992 | (WO) . |
| WO 95/10623 | 4/1995 | (WO) . |
| WO 95/14785 | 6/1995 | (WO) . |
| WO 95/25807 | 9/1995 | (WO) . |

OTHER PUBLICATIONS

N.M. Albert, "Laser Angioplasty and Intracoronary Stents: Going Beyond the Balloon", *AACN: Clinical Issues*, 5, 15–20 (1994).

M.B. Bailie et al., "Vascular–Access–Port Implantation for Serial Blood Sampling in Conscious Swine", *Laboratory Animal Science*, 36, 431–433 (1986).

R.W. Barbee et al., "Retroviral Suicide Vector Does Not Inhibit Neointimal Growth In A Porcine Coronary Model Of Restenosis", *Biochem. Biophys. Res. Comm*, 207, 89–98 (1995).

M. Baringa, "Gene Therapy for Clogged Arteries Passes Test in Pigs", *Science*, 265, 738 (1994).

P. Cameliet et al., "Gene targeting and gene transfer studies of the plasminogen/plasmin system: implications in thrombosis, hemostasis, neointima formation, and atherosclerosis", *FASEB*, 9, 934–938 (1995).

M.W. Chang et al., "Adenovirus–mediated Over–expression of the Cyclin/Cyclin–dependent Kinase Inhibitor, p21 Inhibits Vascular Smooth Muscle Cell Proliferation and Neointima Formation in the Rat Carotid Artery Model of Balloon Angioplasty", *J. Clin. Invest.*, 96, 2260–2268 (1995).

M.W. Chang et al., "Cytostatic Gene Therapy for Vascular Proliferation Disorders with a Constitutively Active Form of the Reinoblastoma Gene Product", *Science*, 267, 518–522 (1995).

G.D. Chapman, "Gene Transfer Into Coronary Arteries of Intact Animals With a Percutaneous Balloon Catheter", *Circ. Research*, 71, 27–33 (1992).

M. Cotton et al., "High–Efficiency receptor–mediated delivery of small and large (48 kilobase gene constructs using the endosome–disruption activity of defective or chemically inactivated adenovirus particles", *Proc. Natl. Acad. Sci.*, 89, 6094–6098 (1992).

J. Dalesandro et al., "Cardiac and Pulmonary Replacement. Gene Therapy for Donor Hears: Ex Vivo Lipsome—Mediated Transfection", *J. of Thoracic and Cardiovascular Surgery*, 111, 416–422 (1996).

D.A. Dichek et al., "Seeding of Intravascular Stents With Genetically Engineered Endothelial Cells", *Circulation*, 80, 1347–1353 (1989).

V.J. Dzau et al. "Gene therapy for cardiovascular disease", *TIBTECH*, 11, 205–210 (1993).

M.Y. Flugelman, "Inhibition of Intravascular Thrombosis and Vascular Smooth Muscle Cell Proliferation by Gene Therapy", *Thrombosis and Haemostasis*, 74, 406–410 (1995).

B.A. French et al., "Persistence of Luciferase Gene Expression Following Adenovirus–Mediated In Vivo Direct Gene Transfer Into Porcine Coronary Arteries", *J. Cell. Biochem.*, Abstract No. DZ 402, 241 (1994).

D.R. Holmes et al., "Polymeric Stenting in the Porcine Artery Model: Differential Outcome of Exogenous Fibrin Sleeves Versus Polyurethane–Coated Stents", *J. American College of Cardiology*, 24, 525–531 (1994).

(List continued on next page.)

*Primary Examiner*—Deborah Crouch
*Assistant Examiner*—Carrie Stroup
(74) *Attorney, Agent, or Firm*—Daniel W. Latham; Harold R. Patton

(57) ABSTRACT

This invention relates to an intraluminal stent having a lumen-wall contacting surface and a lumen-exposed surface wherein the stent comprises a first polymer composition comprising fibrin and wherein the stent is suitable to deliver virus to the wall of a lumen of the body. The invention also relates to methods for making the stent and to methods for delivering nucleic acid to cells accessible from a wall of a body lumen.

20 Claims, 1 Drawing Sheet

OTHER PUBLICATIONS

Y. Kaneda et al., "Increased Expression of DNA Cointroduced with Nuclear Protein in Adult Rat Liver", *Science*, 243, 375–378 (1989).

Y. Kaneda et al., "Introduction and Expression of the Human Insulin Gene in Adult Rat Liver". *J. of Biological Chemistry*, 264, 12126–12129 (1989).

A. Lafont et al., "Which gene for which restenosis?", *The Lancet*, 346, 1442–1443 (1995).

C. Landau et al., "Adenoviral mediated gene transfer to atherosclerotic arteries after balloon angioplasty", *Am. Heart J.*, 129, 1051–1057 (1995).

A.M. Lincoff et al., "Intracoronary Stenting Compared With Conventional Therapy for Abrupt Vessel Closure Complicating Coronary Angioplasty: A Matched Case–Control Study", *J. American College of Cardiology*, 21, 886–875 (1993).

A.M. Lincoff et al., "Local Drug Delivery for the Prevention of Restenosis", *Circulation*, 90, 2070–2084 (1994).

M.J. Mann et al., "Genetic engineering of vein grafts resistant to atherosclerosis", *Proc Natl. Acad. Sci. USA*, 92, 4502–4506 (1995).

W. Mazur et al., "Coronary Restenosis and Gene Therapy", *Texas Heart Institute J.*, 21, 104–111 (1994).

W. Mazur et al., "Replication—Deficient Adenoviral Vectors Mediate Efficient Direct In Vivo Gene Transfer Into Normal and Injured Porcine Coronary Arteries", *J. Cell. Biochem.*, Abstract No. DZ 410, 243 (1994).

Morishita et al. "Novel and Effective Gene Transfer Technique for Study of Vascular Renin Angiotensin System", *J. of Clinical Investigation*, 91, 2580–2585 (1993).

E.G. Nabel, "Gene Therapy for Cardiovascular Disease", *Circulation*, 91, 541–548 (1995).

T. Ohno et al., "Gene Therapy for Vascular Smooth Muscle Cell Proliferation After Arterial Injury", *Science*, 265, 781–784 (1994).

L. Qin et al., "Multiple Vectors Effectively Achieve Gene Transfer In A Murine Cardiac Transplantation Model", *Transplantation*, 59, 809–816 (1995).

Y. Sawa et al., "Efficiency of In Vivo Gene Transfection Into Transplanted Rat Heart by Coronary Infusion of HVJ Liposome", *Circulation(supplement)*, 92, II–479–II–482 (1995).

G. Soldani et al., "Bioartificial polymeric materials obtained from blends of synthetic polymers with fibrin and collagen", *Intl. J. of Artificial Organs*, 14, 295–303 (1991).

P.G. Steg et al., "Arterial Gene Transfer to Rabbit Endothelial and Smooth Muscle Cells Using Percutaneous Delivery of an Adenoviral Vector", *Circulation*, 90, 1648–1656 (1994).

D.J. Stephan et al., "A New Cationic Liposome DNA Complex Enhances the Efficiency of Arterial Gene Transfer In Vivo", *Human Gene Therapy*, 7, 1803–1812 (1996).

J.F. Tanguay et al., "Current Status of Biodegradable Stents", *Contemporary Interventional Techniques*, 12, 699–713 (1994).

H.M.M. van Beusekom et al., "Synthetic polymers as an alternative to metal in stents? In vivo and mechanical behaviour of polyethylene–terephtalate", *Circulation(supplement)*, 86, Abstract No. 2912, I–731 (1992).

Z–Y. Yang et al., "Role of the p21 cyclin–dependent kinase inhibitor in limiting intimal call proliferation in response to arterial injury", *Proc. Natl. Acad. Sci. USA*, 93, 7905–7910 (1996).

THERAPEUTIC INTRALUMINAL STENTS

This is a division of application Ser. No. 08/746,404, filed Nov. 8, 1996, (issued Nov. 10, 1998), now U.S. Pat. No. 5,833,651 which is incorporated herein by reference.

FIELD OF THE INVENTION

This invention relates to devices to deliver therapeutic substances to a lumen wall and in particular, this invention relates to intraluminal stents.

BACKGROUND OF THE INVENTION

Restenosis is the closure of a peripheral or coronary artery following trauma to the artery. Restenosis is believed to be a natural healing reaction to the injury of the arterial wall that is caused by angioplasty procedures. The healing reaction begins with the clotting of blood at the site of the injury. The final result of the complex steps of the healing process is intimal hyperplasia, the migration and proliferation of smooth muscle cells, until the artery is again stenotic or occluded. Restenosis is most often caused by efforts to open an occluded portion of an artery, such as, for example by dilation, ablation, atherectomy or laser treatment. For angioplasty procedures, restenosis occurs at a rate of about 20–50% depending on the vessel location, lesion length, severity of injury, individual propensities to wound healing, the elastic character of a particular vessel, and the like.

Intravascular stents have been disclosed to prevent restenosis. Intravascular stents are medical implants, typically in the form of a hollow cylinder, that are positioned against a body lumen. Metallic intravascular stents are generally permanently implanted in coronary or peripheral vessels. Metal stent designs include those of U.S. Pat. No. 4,733,665 to Palmaz, U.S. Pat. No. 4,800,882 to Gianturco or U.S. Pat. No. 4,886,062 issued to Wiktor. Polymeric stents are also known and both metal and polymeric stents include self-expanding types of stents or balloon-expandable stents. The stent is typically inserted by catheter into a vascular lumen and expanded into contact with the diseased portion of the arterial wall to position the stent and provide internal support for the lumen. Even with the stent in place, restenosis can occur and the stent itself can cause undesirable local thrombosis.

To alleviate the problems associated with stents, anticoagulant substances such as heparin and thrombolytic agents have been incorporated into the stent. These patents include, for example, U.S. Pat. Nos. 5,419,760; 5,342,621; 5,380,299; 5,429,634; 5,304,121; and 5,383,928. Stents have also been prepared from bio-compatible materials including bio-stable or bioabsorbable polymers. U.S. Pat. No. 5,510,077 discloses an intraluminal stent comprising fibrin.

Stents have been used as delivery vehicles for drugs. The stent delivers drug at the site of contact with the vasculature. Local delivery is advantageous in that the effective local concentration of delivered drug is much higher than can normally be achieved by systemic administration. The use of stents for drug delivery is discussed in U.S. Pat. No. 5,102,417 to Palmaz and in international patent applications WO 91/12779 and WO 90/13332. These applications suggest that antiplatelet agents, anticoagulant agents, antimicrobial agents, antimetabolic agents and other drugs could be supplied by stent to reduce the incidence of restenosis. U.S. Pat. No. 5,464,650 discloses the application of solvent with a drug and a polymer to the body of a stent to deliver drugs to a vessel wall. Drug delivery is necessary for the treatment of some diseases; however, a concern related to the use of stents for drug delivery is that drug delivery may not be sustainable from a stent. Over time the drug concentration on the stent may be diluted out, through drug inactivation, degradation, dilution into the adjacent lumen or reduced through delivery to the surrounding tissues.

Stents seeded with endothelial cells (Dichek, et al. *Circulation* 80:1347–1353, 1989) are disclosed as a method for delivering recombinant protein over time to the vascular wall. This method requires autologous cells. The endothelial cells need to sustain delivery of the protein at concentrations that will be therapeutically effective to the cells of the lumen wall. The excreted protein concentration produced by the endothelial cells that is required to treat the surrounding vascular tissue can be quite high. Moreover, the endothelial cells are likely to die out in the absence of surrounding supportive tissue. Improved methods for the sustainable delivery of therapeutic protein(s) and nucleic acid are needed.

Viruses are useful vehicles for gene delivery. A variety of genetically modified viruses are known in the art. For example, there are a variety of RNA and DNA based viruses that are useful for gene delivery. Adenoviruses are particularly useful as gene delivery vehicles. The virus particle is relatively stable and the adenovirus genome does not undergo rearrangement at a high rate.

Catheters have been used to deliver liposomes and viruses to the vascular wall. Chang, et al (*Science* 267:518–522, 1995) disclose the use of a catheter to deliver an adenoviral vector encoding the retinoblastoma gene product to an injured vessel wall. International patent application WO 95/25807 to Nabel et al. and Ohno et al. (*Science* 265:781–784, 1994) discloses the delivery of an adenoviral vector to blood vessel cells using an angioplasty balloon catheter.

The duration of exposure to gene transfer reagents to the vascular wall is likely to be an important variable in the effectiveness of gene delivery to cells lining lumen walls. Lumens that support rapid unidirectional fluid flow (i.e., in one example, the coronary arteries) cannot be occluded, yet these tissues need sustained exposure to gene transfer reagents for effective nucleic acid delivery. Ohno et al. (supra) used a balloon angioplasty catheter to administer virus to a blood vessel lumen of the leg. The balloon catheter was positioned in the vessel, occluding blood flow for twenty minutes. Balloon catheters generally block fluid flow and cannot be held in place for prolonged periods to facilitate gene transfer. Balloon catheters cannot be used for gene therapy in coronary arteries or other tissues facilitating rapid fluid flow. Even in areas where there is not heavy unidirectional fluid flow, it is unlikely that catheters can be held in place in vivo for extended periods to facilitate gene transfer without patient discomfort or without surgical procedures that require general anesthesia. These problems have been recognized in the art, as disclosed by Baringa (*Science* 265:738, 1994).

A device that directly contacts the injured or damaged tissue in need of gene transfer therapy for extended periods of time is needed, but these devices should not interfere with lumen function. Contact of a bare device, such as a catheter loaded with virus, may not provide the long term contact necessary to maximize gene transfer. Moreover, virus is washed from the catheters as they move through the vasculature to the site of vessel injury and this diluting effect reduces the efficiency of gene transfer from these devices. Free unassociated virus can also pose a risk for widespread uncontrolled gene delivery.

SUMMARY OF THE INVENTION

This invention relates to the use of stents to deliver virus to the wall of a lumen for gene delivery. The device of this invention is preferably an intraluminal stent comprising a lumen-wall contacting surface, a lumen-exposed surface, a first polymer composition comprising fibrin, the composition covering at least a portion of the lumen-wall contacting surface of the stent, and a virus to deliver nucleic acid to a cell wherein the virus is associated with the first polymer composition covering the lumen-wall contacting surface.

The first polymer composition preferably includes a polymer or copolymer that is viscoelastic, tear-resistant, biocompatible and preferably nonthrombogenic. The first polymer composition is preferably capable of dehydration and rehydration.

The first polymer composition can include a fibrin polymer or a combination of a fibrin polymer and another polymer including, for example, alginate, collagen, hyaluronic acid, polyurethane and cellulose.

In one embodiment, the virus in the intraluminal stent is an adenovirus and in another embodiment the virus is a retrovirus. The nucleic acid delivered by the virus is preferably capable of directing and expression of a protein in a cell. In another embodiment, the nucleic acid delivered by the virus capable of binding to nucleic acid within a cell. In one embodiment the nucleic acid is RNA and in another embodiment the nucleic acid is DNA.

The device can also include a second polymer composition covering at least a portion of the first polymer composition on the lumen wall-contacting surface and can also optionally include a third polymer composition covering at least a part of the lumen-exposed surface of the stent. Preferably the second polymer composition is biodegradable and in one embodiment the second polymer composition also comprises fibrin. In one embodiment the second polymer composition comprises polylactic acid. The second polymer composition can further comprise an anti-inflammatory compound and in one embodiment the anti-inflammatory compound is a cyclosporin.

In another embodiment of this invention, the stent includes a first polymer composition comprising fibrin and another polymer composition covering at least a part of the lumen-exposed surface of the stent. The polymer composition covering the lumen-exposed surface of the stent is preferably negatively charged and in one embodiment the negatively charged polymer composition is selected from the group consisting of a mucopolysaccharide, dextran-sulfate, an acrylic acid polymer, polyinosinic acid and heparin, or a polymer composition comprising a combination thereof.

In another aspect of this invention the invention relates to a method for delivering nucleic acid to cells accessible from a wall of a body lumen comprising the steps of providing a stent comprising a lumen-wall contacting surface, a lumen-exposed surface, a first polymer composition comprising fibrin covering at least a portion of the lumen-wall contacting surface to form a polymer covered stent, and virus associated with the first polymer composition wherein the stent is capable of delivering nucleic acid to cells accessible from a wall of a body lumen. The method also includes the steps of positioning the stent in a lumen of the body and contacting the lumen-wall contacting surface of the stent with the wall of a lumen of the body. The lumen wall contacting surfaces contemplated in this invention include a blood vessel, the wall of a lymph vessel, an intestine, a respiratory airway and others. Preferably the stent is introduced into the lumen of the body using a catheter or by surgical implantation.

In yet another aspect of this invention, the invention relates to a method for making a stent to deliver nucleic acid to cells accessible from a wall of a body lumen comprising the steps of; providing a stent comprising a lumen-wall contacting surface, a lumen-exposed surface, and a first polymer composition comprising fibrin covering at least a portion of the lumen-wall contacting surface to form a polymer covered stent; preparing virus capable of delivering nucleic acid to the walls of a body lumen; and loading the virus on the first polymer composition.

In a preferred embodiment, the loading step comprises dipping the polymer coated stent into a solution or gel comprising the virus, spraying the polymer coated stent with a solution comprising the virus, wicking a solution comprising the virus onto the polymer coated stent, loading the first polymer composition and virus into a mold, and other methods.

In a preferred embodiment of this method the virus is added to the stent just prior to stent implantation and in another embodiment the stent is covered with a second polymer composition covering at least a portion of the lumen-exposed surface. The covering step can be performed either before or after the loading step. Optionally the virus coated stent can be covered with a biodegradable polymer composition on at least a portion of the lumen-wall contacting surface of the stent.

This invention also relates to a kit comprising a stent comprising a lumen-wall contacting surface, a lumen-exposed surface and a first polymer composition comprising fibrin covering at least a portion of the lumen-wall contacting surface of the stent; a virus loading solution to be applied to the stent; and a container to house the stent and the solution during application of the virus loading solution.

The invention also relates to a virus delivery system comprising a polymer composition comprising fibrin; and virus capable of delivering nucleic acid to a cell.

BRIEF DESCRIPTION OF THE PREFERRED EMBODIMENTS

Figure 1:
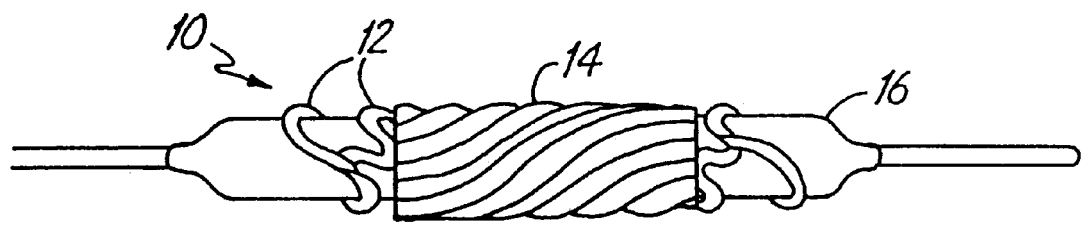
FIG. 1 is an elevational view of a preferred balloon catheter with stent including a first polymer fibrin composition, according to the present invention.

The stent and methods of this invention are designed to sustainably deliver virus to cells accessible to a body lumen to treat or prevent disease. The present invention provides an easily manufactured, easily assembled and easily deliverable system.

The term "disease" as used herein denotes genetic or acquired disease, as well as conditions or disorders that may or may not have a genetic component (including, but not limited to, stenosis, myocardial infarction, aneurysm, atherosclerosis, as well as diseases not necessarily associated with the vasculature, including, but not limited to muscular dystrophy, cystic fibrosis, digestive disorders, cancer, inherited disease, colitis, benign prostatic hypertrophy, etc.)

In particular, the term "disease" includes trauma or injury that is incidental to surgery or other treatment including the deployment of the stent. In addition, the methods of this invention may be performed in anticipation of "disease" or as a prophylactic. A prophylactic treatment is one that is provided in advance of any symptom of disease in order to prevent disease, prevent progression of disease or attenuate any subsequent onset of a symptom of such disease.

The term "capable of directing and expressing a protein in a cell" indicates that the nucleic acid associated with the virus is capable of directing transcription and translation of at least one protein encoded by the nucleic acid when the nucleic acid is introduced into the cellular milieu. As used in this disclosure, the term "protein" includes protein, polypeptide and peptides that can be expressed as translation products from mRNA.

The term "pharmaceutically acceptable" refers to a material that is not biologically or otherwise undesirable. The material can be administered along with the virus of this invention without causing undesirable biological effects nor does the material interact in a deleterious manner with the virus or the luminal stents of this invention, nor with any other component of the pharmaceutical composition in which it is contained.

The term "fibrin" is used herein to refer to the naturally occurring or recombinant polymer of fibrinogen that arises during blood coagulation.

The term "cells accessible from the walls of a vessel lumen" refers to the cells lining a lumen wall in the body and therefore directly accessible to the virus delivered by the device of this invention; as well as cells normally found beneath the cells lining a lumen wall that, because of local disruption to the lumen wall, are now directly accessible to the virus delivered by the device of this invention; cells migrating into the wounded area; and, cells indirectly accessible to the virus delivered by the device of this invention either because the virus is able to infect these cells or because the nucleic acid is transferred to these cells.

The term "sustained" is used herein to refer to the ability of the virus associated with nucleic acid to mediate its delivery function from the stent to cells accessible from the walls of a body lumen over time. Preferably, the virus is able to delivery the nucleic acid to the cells accessible from the walls of a body lumen for at least about 24 hours.

The term "stent" refers to any device capable of being delivered by a catheter which when placed into contact with a portion of a wall of a lumen to be treated will also place virus at the lumen wall. The stent has a lumen wall-contacting surface and a lumen-exposed surface. Where the stent is shaped generally as a tube-like structure, including a discontinuous tube or a ring-like structure, the lumen-wall contacting surface is the outside surface of the tube and the lumen-exposed surface is the inner surface of the tube. The stent can include polymeric, metallic or polymeric and metallic structural elements onto which a first polymer composition comprising fibrin is applied.

A deformable metal wire stent useful as a stent framework to support the virus-laden fibrin composition of this invention includes U.S. Pat. No. 4,886,062 to Wiktor and this patent discloses preferred methods for making a wire stent. Other metallic stents useful in this invention include those of U.S. Pat. No. 4,733,665 to Palmaz and U.S. Pat. No. 4,800,882 to Gianturco. FIG. 1 of this invention provides an elevational view of a preferred stent 10 of this invention prepared according to the methods of U.S. Pat. No. 4,886,062. The stent comprises a stent framework 12 with a fibrin covering 14 extending circumferentially around at least a portion of the lumen-wall contacting surface of the stent and preferably extending over substantially all of the lumen-wall contacting surface. A balloon 16 is positioned in FIG. 1 adjacent the lumen-exposed surface of the stent to facilitate delivery of the stent. The stent of U.S. Pat. No. 4,886,062 can be modified to increase or to decrease the number of wires provided per cm. Similarly, the number of wire turns per centimeter can also be modified to produce a stiffer or a more flexible stent framework.

Polymeric stents can also be used in this invention. The polymers can be nonbioabsorbable or bioabsorbable in part, or total. Stents of this invention can be completely nonbioabsorbable, totally bioabsorbable or a composite of bioabsorbable polymer and nonabsorbable metal or polymer. For example, another stent suitable for this invention includes the self-expanding stent of resilient polymeric material as disclosed in international patent application WO 91/12779.

Nonbioabsorbable polymers can be used as alternatives to metallic stents. The stents of this invention should not substantially induce inflammatory and neointimal responses. Examples of biostable nonabsorbable polymers that have been used for stent construction with or without metallic elements include polyethylene terephthalate (PET), polyurethane urea and silicone (for example, see van Beusekom et al. *Circulation* 86(suppl I):I-731, 1992 and Lincoff et al. *J. Am. Coll Cardiol* 21 886–887, 1993.

Bioabsorbable polymers have also been used for stents. Polymers that are biodegradable should be biocompatible. The rate of degradation is generally related to the permeability of the polymer, the solubility of the polymer in water, the crystallinity and the physical dimensions of the polymer. Types of bioabsorbable polymers include polyesters and polyorthoesters including polylactic acid and polyglycolic acid. Polylactic acid can include poly-L-lactic acid (PLLA), poly D,L-lactic acid and poly-D-lactic acid. Polyanlydrides can also be used and they can be modified by varying the monomer ratios in polyanhydride copolymers to become surface eroding. Other bioabsorbable polymers include, but are not limited to, polyphosphate esters, polyaminocarbonates, polyhydroxybutyrates and hyaluronic acid polymers. For a review of bioabsorbable polymers contemplated in this intention see Tanquay et al. (*Contemp. Intervention. Tech.* 12(4):699–713, 1994).

Other stents that could be or covered with the fibrin-containing compositions of this invention for virus delivery include the Palmaz-Schatz coronary Stent (Johnson & Johnson Interventional, Warren, N.J.) and stents from memory shaped metals such as self-expanding nitinol stents including the Cardiocoil™ stent (Medtronic, Eden Prairie, Minn. and disclosed in U.S. Pat. No. 5,372,600). The stents used in this invention should be flexible to navigate lumens during insertion, biocompatible and reliably expand and embed in the lumen wall.

The stents of this invention are or covered with a first polymer composition comprising fibrin to provide sustained release of virus at the lumen wall contacting surface where the stent is positioned. The first polymer composition of this invention can be prepared from a single polymer, as a copolymer, representing two different repeating polymeric units or as a composition comprising fibrin alone with one or more polymers or one or more other proteins. The composition preferably forms a viscoelastic, tear-resistant biocompatible polymer. The term "viscoelastic" refers to the pre-scribed "memory" characteristics of a molecule that allow the molecule to respond to stress as if the molecule was a combination of elastic solids and viscous fluids. The term "tear resistent" indicates that when the fibrin polymer is exposed to expansion stress, the material does not substantially tear. Tearing refers to the propagation of a nick or cut in the material while under stress. When the stent of this invention is expanded on a balloon, the fibrin is able to expand to accommodate the balloon expansion. The term "biocompatible" is used herein to refer to a material that does not have toxic or injurious effects on biological systems.

Preferably the first polymer composition minimizes or does not exacerbate irritation to the lumen wall when the stent is in position. The first polymer composition is preferably nonthrombogenic when applied alone or alternatively when used with anti-thrombogenic agents such as heparin, and the like or with anti-inflammatory agents such as cyclosporins, and the like. The first polymer composition is also preferably a biostable or a bioabsorbable polymer depending on the desired rate of release or the desired degree of polymer stability. The features of bioabsorbability were discussed above in the discussion related to bioabsorbable polymers used in stents.

The stent of this invention is or covered with a composition comprising fibrin. The stents of this invention can be coated, as one example, according to U.S. Pat. No. 5,510,077 including for example, polymerization of fibrin on a metal or polymeric framework by application of a fibrinogen solution and a solution of a fibrinogen-coagulating protein or by attachment of a fibrin preform or sleeve such as an encircling film of fibrin, including the film provided in U.S. Pat. No. 4,548,736 to Muller.

As described in U.S. Pat. No. 4,548,736 and in U.S. Pat. No. 5,510,077, fibrin is clotted by contacting fibrinogen with a fibrinogen-coagulating protein such as thrombin. The fibrin in the fibrin-containing stent preferably also has Factor XIII and calcium present during clotting as described in U.S. Pat. No. 3,523,807 to Gerendas and European Patent Application 0366564.

As outlined in U.S. Pat. No. 5,510,077, preferably the fibrinogen used to make the fibrin is a bacteria-free and virus-free fibrinogen such as that described in U.S. Pat. No. 4,540,573 to Neurath et al. In one embodiment, the fibrinogen is preferably used in solution with a concentration of about 10 to about 50 mg/ml with a pH of about 5.89–9.0 and with an ionic strength of about 0.05 to 0.45. The fibrinogen solution typically contains proteins and enzymes such as albumin, fibronectin (0–300 $\mu$g per ml fibrinogen), Factor XIII (0–20 $\mu$g per ml fibrinogen), plasminogen (0–210 $\mu$g per ml fibrinogen), antiplasmin (0–61 $\mu$g per ml fibrinogen) and Antithrombin III (0–150 $\mu$g per ml fibrinogen). The thrombin solution added to make the fibrin is typically at a concentration of about 1 to 120 NIH units/ml with a preferred concentration of calcium ions between about 0.02 and 0.2M.

Also preferably, the fibrinogen and thrombin used to make fibrin in the present invention are from the same animal or human species as that in which the stent of the present invention will be implanted to avoid cross-species immune reactions. The resulting fibrin can also be subjected to heat treatment at about 150° C., for about 2 hours to reduce or eliminate antigenicity.

In the Muller patent, the fibrin product is in the form of a fine fibrin film produced by casting the combined fibrinogen and thrombin in a film and removing moisture from the film osmotically through a moisture permeable membrane.

In European Patent Application 0366564, a substrate is contacted with a fibrinogen solution and with a thrombin solution resulting in a fibrin layer formed by polymerization of fibrinogen on the surface of the device. Multiple layers of fibrin applied by this method can provide a fibrin layer in a variety of thicknesses. In the Gerendas patent, the fibrin can be first clotted and then ground into a powder that is mixed with water and stamped into a desired shape in a heated mold. These methods can be used with fibrin monomers or with combinations of monomers to form the first polymer composition of this invention. Those skilled in the art will recognize that the methods for forming the first polymer composition can be modified to include other polymers, as contemplated in this invention, without undue experimentation.

The first polymer compositions of this invention include fibrin or fibrin with another substance, including another polymer. Other polymers include, but are not limited to, albumin, collagen, alginate, polylactic acid, cellulose, hyaluronic acid and polyurethane. An example of a copolymer with improved structural strength and improved biological performance is a fibrin and polyurethane copolymer or a fibrin alginate copolymer. U.S. Pat. No. 5,510,077 discloses a copolymer of fibrin and polyurethane that can be used in the stents of this invention. The copolymer can be used to form the stent or can be used to cover the stent. Since fibrin is more readily degraded in the body than polyurethane, polyurethane can be used to regulate degradation of the fibrin comprising composition covering the stent and to slow virus release from the stent.

Soldani, et al. discloses a crosslinked blend of polyurethane and fibrin for vascular graft material ("Bioartificial Polymeric Materials Obtained from Blends of Synthetic Polymers with Fibrin and Collagen" *International Journal of Artificial Organs*, Vol. 14, No. 5, 1991). This fibrin/polyurethane composition can be used as a coating applied to a stent. Stents with fibrin and polyurethane copolymer can be affixed to the distal end of a catheter in a longitudinally stretched condition causing the stent to decrease in diameter.

The stent can be delivered through the body lumen on the catheter to the treatment site where the stent is released from the catheter to allow it to expand into contact with the lumen wall. A device for deploying such a stent is disclosed in U.S. Pat. No. 5,192,297 issued to Hull. Other self-expanding stent designs, including resilient metal stent designs, could also be used with fibrin either incorporated into the material forming the underlying structure of the stent or alternatively applied as a film and/or a coating onto the stent.

In addition to the first polymer composition of this invention being viscoelastic, tear-resistant and biocompatible, the first polymer composition is preferably substantially nonthrombogenic. That is, the first polymer composition neither causes nor substantially promotes the formation of thrombi. Preferably the coagulating effect of any residual coagulation protein in the fibrin is neutralized before employing fibrin in the stent. This prevents clotting at the fibrin interface with blood after stent implantation. Neutralizing the coagulating effect can be accomplished, for example, by treating the fibrin with irreversible coagulation inhibitor compounds, agents that promote clot degradation, or heat treatment following polymerization. For example, hirudin or D-phenylalanyl-propyl-arginine chloromethyl ketone (PPACK) can be used. Anti-coagulants such as heparin, polyethylene oxide, hirudin and/or tissue plasminogen activator can also be added to reduce the possibility of further coagulation. Those skilled in the art will recognize that all of these compounds have been incorporated into devices or have been used to regulate and prevent clotting activity.

Heparin can be incorporated into the stent prior to implantation in an amount effective to prevent or limit thrombosis. For example, the fibrin stent can be immersed in a solution of heparin within 10–30 minutes prior to implantation. The heparin immersion procedure can be conducted in a heparin solution having a concentration of about 1000–25,000 heparin units/l. The heparin solution can alternatively be added at the time that virus is loaded onto the stent. Heparin can also be incorporated into the fibrin matrix before the fibrin has completely polymerized. For example, after the fibrinogen and thrombin have been combined and the resulting fibrin has been shaped, but within two hours of combining the fibrinogen and thrombin, the fibrin is immersed in a solution of heparin. Where fibrin polymerization has been largely completed, the fibrin can be immersed in heparin solution containing up to about 20,000 units/ml of heparin without damaging the integrity of the fibrin structure. Immersion times will depend on the concentration of the heparin solution and the concentration of heparin desired in the fibrin. However, preferably, in a solution of heparin having a concentration of about 10,000–20,000 units/ml of heparin, an immersion time of about 12–24 hours may be used. The heparin should be added so that the ratio of heparin to fibrinogen does not lead to a weak fibrin covering. Typically, less than about 50–500 units of heparin can be used in a stent which includes 0.0003–0.0006 grams of fibrin. Alternatively, powdered heparin can be dusted onto the stent during the polymerization process and additional thrombin and fibrinogen can then be applied as a coating over the heparin.

The shape of the fibrin can be modified based on the methods used to cover the stent. Fibrin can be spray coated onto the stent or a fibrin film can be molded over the stent framework. For example, the mixture can be formed into a stent having essentially the same shape as the stent shown in U.S. Pat. No. 4,886,062 to Wiktor. The stent can be formed as a wound wire, as a polymeric or metal framework or the stent made with fibrin can be directly molded into the desired shape. The first polymer composition of this invention can cover both the lumen wall contacting surface and the lumen-exposed surface of the stent. Preferably, the first polymer composition covers at least a portion of the lumen-wall contacting surface of the stent. As one example of a fibrin covering on at least a portion of the lumen-wall contacting surface of a stent, the fibrin can cover the stent as disclosed in U.S. Pat. No. 5,510,077 to Dinh.

In one embodiment of the Dinh patent, a stent is disclosed that includes a porous polymeric sheet material into which fibrin is incorporated. The sheet could be prepared from polyurethane, for example, by dissolving a polyether urethane in an organic solvent such as methyl-2-pyrrolidone; mixing into the resulting polyurethane solution a crystalline particulate material like salt or sugar that is not soluble in the solvent; casting the solution with particulate material into a thin film; and then applying a second solvent, such as water, to dissolve and remove the particulate material, thereby leaving a porous sheet. The porous sheet could then be placed into a fibrinogen solution in order to fill the pores with fibrinogen followed by application of a solution of thrombin and fibrinogen to the surface of the sheet to establish a fibrin matrix that occupies both the surface of the sheet and the pores of the sheet. Preferably, a vacuum would be pulled on the sheet to insure that the fibrinogen applied to the sheet is received into the pores. In another embodiment of the Dinh patent, the stent framework is positioned within a mold and the compounds forming the fibrin polymer are incorporated into the mold. The first polymer composition forming a fibrin sheet or sleeve can be prepared in an extended shape and then compressed or dehydrated into a final shape to fit over the stent such that when the stent is expanded in place to fit the walls of a lumen, the first polymer composition can be readily expanded without tearing or introducing irregularities into the sleeve and/or the coating.

It is also possible to apply the fibrin as a spray. In this example the covering solution includes a fibrin monomer solution that is sprayed or pumped as a liquid over the stent framework. Methods for using a spray application to cover a stent is provided in U.S. Pat. No. 5,464,650 to Berg.

The stents of this invention can have any of a variety of dimensions. Preferred dimensions for intravascular stents include the dimensions provided in U.S. Pat. No. 4,886,062 to Wiktor. As will be recognized by those of ordinary skill in the art, the diameter of the stent can be varied to accommodate different thickness of the polymer compositions of this invention. A smaller stent can be used with a thicker fibrin coating to obtain the same overall diameter of a traditionally sized intravascular stent. In addition, the stents can be modified in their overall length. The length of the stent can be adapted to cover a larger or a smaller surface area as determined either by the lumen location to receive the stent or by the surface area of the lumen to be exposed to the virus.

The stents of this invention are loaded with virus capable of delivering nucleic acid to a cell. Preferably, nucleic acid carried by the virus has a therapeutic or disease-treating effect on cells that are contacted by virus delivering the nucleic acid. The nucleic acid delivered by the virus includes nucleic acid resident within the virus capsid and incorporated during virus assembly in a cell or the nucleic acid delivered by the virus can be associated on an external portion of the virus.

There are a number of viruses, live or inactivate, including recombinant viruses that can be used to deliver nucleic acid to the vessel walls of a lumen. For example, retrovirus can be produced using the system disclosed by Miller et al. (*Mol. Cell Biol.* 10:4239–4242, 1990). Using this method, the ecotropic cell line, Psi2, is transfected with a construct capable of directing expression of a suicide gene, such as the thymidine kinase gene. Virus harvested from the Psi2 cells or from other cells can be used to infect target tissue (see Barbee et al. *Biochem. Biophys. Res. Comm.* 207(1):89–98, 1995). The retrovirus can be genetically modified to deliver any of a variety of genes, including for example, the herpes simplex virus thymidine kinase (HSVtk) gene. In one embodiment where the thymidine kinase suicide gene is used, ganciclovir is administered (Syntex, Palo Alto, Calif.) at a dose of about 5 mg/kg iv for one hour every 12 hours for a two week period in experimental animals as reported by Bailie et al. (*Lab Anim. Sci.* 36(4):431–433, 1986). Herpesviruses have also been used as gene vectors (see for example Weir et al. *Human Gene Therapy* 7:1331–1338, 1996).

Adenoviruses have been used to deliver genes to cells lining vessel walls and Nabel et al. have used an adenoviral vector to deliver the HSVtk gene (international patent application WO 95/25807 to Nabel et al.). In these experiments, a replication-deficient recombinant adenoviral vector, AD.HSV-tk, was constructed by deleting the E3 region of the adenovirus type 5 genome and adding to this end the HSV-tk expression cassette from the plasmid pAD-HSV-tk. The expression cassette contained the HSV-tk gene, the polyoma virus enhancer, and the adenovirus inverted terminal repeat (ITR), encapsidation signal and E1a enhancer region. Adenovirus particles were used to introduce the construct into porcine femoral arteries (Ohno et al. *Science* 265:781–784, 1994).

A variety of adenovirus vectors that would be suitable for introducing a gene into cells accessible from the walls of a vessel lumen are also disclosed in international patent application WO 94/27612 to French, et al., international patent application WO 95/10623 to Finkel et al., international patent application WO 96/01902 to Bohme et al., Landau et al. (*Am. Heart Journal* 129:1051–1057, 1995), and Steg et al. (*Circulation* 90:1648–1656, 1994). Adenovirus has been used in a variety of experiments to deliver nucleic acid capable of directing and expressing protein in a cell. These include, but are not limited to, human p21 (*J. Clin. Invest.* 96(5):2260–2268, 1995), the retinoblastoma gene (*Science* 267:518–22, 1995), cytosine deaminase (*Proc. Natl. Acad. Sci. (USA)* 91(22):10732–10736, 1994), antisense oligonucleotides (international patent application 9605321), c-myc (*Gene Therapy* 2:675, 1995), superoxide dismutase, tissue plasminogen activator, interleukin-10 (*Transplantation* 59(6):809–816, 1995), antisense CDC2 (*Proc. Natl. Acad. Sci. (USA)* 92(10):4502–4506, 1995), and soluble VCAM.

Other viruses can be used to deliver nucleic acid to cells accessible from the walls of a vessel lumen. Hemagglutinating Virus of Japan (HVJ or Sendai virus) has been used for gene delivery. In this method foreign DNA is complexed with liposomes, a nuclear protein and the HVJ viral protein coat. It is known that cationic liposomes can help recombinant virus infection (see for example, Dalesandro, J. et al. *J. Thoracic and Cardiovascular Surgery* 111(2):416–422, 1996). Complexes of inactivated hemagglutinating virus of Japan (HVJ) and liposomes were shown to improve transfection efficiency (see *J. Clin. Invest.* 91:2580–2585, 1993). The HVJ method has been used for gene transfer in the liver, the kidney and the vascular wall (see Kaneda, et al. *Science* 243:375–378, 1989; Kaneda et al. *J. Biol. Chem.* 264:12126–12129, 1989; Kato et al. *J. Biol. Chem.* 266:3361–3364 and Morishita et al. *J. of Clin. Invest.* 91:2580–2585, 1993). The liposomes can be incorporated into the polymer coated stent either during polymer coating or after polymer coating, as a separate application.

Those skilled in the art will recognize that the virus used in this invention should be stable enough to infect cells after the virus has been associated with a stent and transported in vivo to the delivery sight. Moreover, the virus should be stable at body temperatures for greater than about 24 hours to provide sustained delivery of the virus to the walls of the lumen.

The virus on the stent is capable of delivering nucleic acid to a cell accessible from the walls of a vessel lumen. Exemplary nucleic acid that would function as nucleic acid delivered by the virus using the stent device of this invention include, but are not limited to, nucleic acid operably encoding a protein, polypeptide, or peptide to deliver a therapeutic effect to a cell. The nucleic acid can include an entire gene or a portion of a gene. Exemplary genes include, but are not limited to, the active form of the retinoblastoma gene (see Lafont et al. *Lancet* 346:1442, 1995 and references cited therein); nitric oxide synthase (a protein that is known to relax blood vessels and prevent clot formation); p21 protein (Chang et al. *J. Clin. Invest.* 96:2260–2268, 1995); prostaglandin H synthase (to restore an endogenous inhibitor of platelet aggregation and vasoconstriction following injury to endothelium); genes inducing chemosensitivity; such as, for example, the introduction of suicide genes into localized regions of a lumen to inhibit cell proliferation or induce cell death for restenosis or as a cancer treatment; genes encoding growth factors or cytokines to treat proliferative disorders, vascular repair, injury, and the like. In addition the nucleic acid contained in the recombinant virus may include or encode sense and/or antisense nucleic acid strands to inhibit or to promote gene expression.

Oligonucleotides, such as antisense oligonucleotides, can also be delivered by the virus to limit expression of a gene in a cell. Oligonucleotides can be used to inhibit expression of protein, including, but not limited to anti-cdc2 kinase, proliferating cell nuclear antigen (PCNA), c-myb and/or c-myc.

There are a variety of disorders that can be treated using the stents of this invention. The disorders can be treated either by the expression of a gene to provide a therapeutic effect to a cell, expression of a gene to replace a mutated gene in a cell, to augment expression of a protein in a cell or to inhibit expression of a gene in a cell. Examples of these disorders include, but are not limited to, cell proliferation resulting from stenosis (for example using suicide genes or targeting cell-cycle regulatory genes); damage associated with myocardial infarction or aneurysms (targeting fibroblast growth factor or transforming growth factor β and protease respectively); atherosclerosis (for example, targeting high density lipoprotein); familial hypercholesterolemia (targeting the low density lipoprotein receptor), hypercoagulable states (targeting tissue-plasminogen activator), refractory diabetes mellitus (for example, targeting insulin) as well as diseases not necessarily associated with the vasculature, including, but not limited to, muscular dystrophy, cystic fibrosis, digestive disorders, cancer, inherited disease, colitis, benign prostatic hypertrophy, transplant rejection or transplant vasculopathy (targeting for example, leukocyte adhesion molecule or cytokines respectively), and the like.

The gene sequence of the nucleic acid delivered by the virus, including nucleic acid encoding proteins, polypeptide or peptide is available from a variety of sources including GenBank (Los Alamos National Laboratories, Los Alamos, N.M.), EMBL databases (Heidelberg, Germany), and the University of Wisconsin Biotechnology Center, (Madison, Wis.), published journals, patents and patent publications. All of these sources are resources readily accessible to those of ordinary skill in the art. The gene sequence can be obtained from cells containing the nucleic acid fragment (generally, DNA) when a gene sequence is known. The nucleic acid can be obtained either by restriction endonuclease digestion and isolation of a gene fragment, or by polymerase chain reaction (PCR) using oligonucleotides as primers either to amplify cDNA copies of mRNA from cells expressing the gene of interest or to amplify cDNA copies of a gene from gene expression libraries that are commerically available. Oligonucleotides or shorter DNA fragments can be prepared by known nucleic acid synthesis techniques and from commercial suppliers of custom oligonucleotides such as Amitof Biotech Inc. (Boston, Mass.), or the like. Those skilled in the art will recognize that there are a variety of commercial kits available to obtain cDNA from mRNA (including, but not limited to Stratagene, La Jolla, Calif. and Invitrogen, San Diego, Calif.). Similarly, there are a variety of commercial gene expression libraries available to those skilled in the art including libraries available form Stratagene, and the like. General methods for cloning, polymerase chain reaction and vector assembly are available from Sambrook et al. eds. (*Molecular Cloning: A Laboratory Manual*, 1989 Cold Spring Harbor Laboratory Press, Cold Spring Harbor, N.Y.) and Innis, et al. eds. (*PCR Strategies*, 1995, Academic Press, New York, N.Y.).

Depending on the maximum genome size that a particular viral genome can accommodate or that can be associated with a virus particle, the virus delivering nucleic acid to the cell can include nucleic acid encoding one or more proteins, polypeptides or peptides. Oligonucleotides can be delivered by virus through the incorporation of oligonucleotides within the virus or associated with the outer surface of the virus using the methods employed to deliver HVJ to cells (supra).

Figure 2:
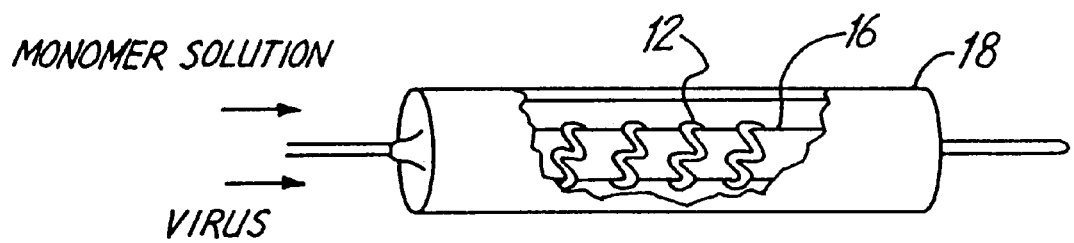
FIG. 2 illustrates a method of making a virus-loaded, first polymer composition comprising fibrin-covered stent using a mold.

The stent can be loaded with virus by mixing the monomer solution of the first polymer composition with virus or by directly applying the virus to the polymerized composition. In a first embodiment, the stent is loaded with virus at the time of formation of the first polymer composition. FIG. 2 provides an example where a stent is formed over a balloon and introduced into a mold to receive a solution sufficient to form the first polymer composition and including virus to be incorporated into the first polymer coating. In FIG. 2, the stent framework 12 is positioned over the balloon 16 and introduced into a mold 18. A monomer solution capable of forming a first polymer composition is introduced into the mold with virus. Once the polymer is formed over the stent framework 12, the stent is released from the mold. The virus can also be included in a monomer solution as a spray or liquid coating to be applied to the stent framework.

Alternatively, the virus can be added to the polymer coated stent either at the time of stent manufacture or by the physician, prior to stent implantation. Where the first polymer composition is capable of dehydration and rehydration, the fibrin coated stent can be supplied in a sterile, dehydrated form and virus is loaded onto the stent by rehydration of the first polymer composition positioned on the stent framework by emersing, wicking or spraying a liquid suspension (such as a balanced salt solution, including HBSS or a tissue culture media, and the like) containing the virus onto the stent prior to stent implantation. The liquid used to deliver virus to the first polymer coating should support the stability of the virus and should included pH buffered solutions, stabilizers such as albumin, glycerol, or the like in a form that is biocompatible and preferably nonimmunogenic.

In one embodiment, the dehydrated first polymer covered stent is rehydrated in a calcium chloride solution and a sodium alginate solution comprising the virus and the solution is sprayed onto the fibrin stent. A layer of calcium alginate precipitates onto the surface with the virus. Alternatively the first polymer composition covering can be rehydrated in a solution of sodium alginate with virus and a layer of calcium alginate is sprayed or otherwise coated over the first polymer covering now incorporating virus. Where the virus is dissolved in a polymer solution for spray application or air pump applications, the polymer should be of sufficiently low viscosity to facilitate the application of the solution to the stent.

Fibrin has a number of features that make it particularly suited for sustained gene delivery. Fibrin has holes, gaps and spaces that support and provide room for the virus. Virus entering the fibrin mesh moves to the lumen-wall contacting surface of the stent as fluid moves through the lumen-exposed surface of the stent. Fibrin is capable of dehydration and rehydration making a fibrin covered stent suitable for loading virus in a liquid suspension. Fibrin is also biodegradable and fibrin biodegradation on a fibrin/virus-coated stent further facilitates virus contact with the lumen wall. The polymer composition comprising fibrin and virus provide a unique stabilizing composition for gene delivery.

The stents of this invention are useful for the introduction of virus to a body lumen surface. For example, the stents of this invention can be introduced into vessels and tubular elements of the body, including, but not limited to, blood vessels of the heart, brain, limbs, gut and kidneys; lymphatic vessels; tubular elements of the male and female reproductive system, the urinary system or the gastrointestinal system, including the esophagus and the intestines. Other lumens that can receive a stent of this invention include the lung including the bronchi, trachea, bronchioles, etc., the bladder and the liver.

Methods for introducing a stent into a lumen of a body are well known and the virus-loaded stents of this invention are preferably introduced using a catheter. As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing a first polymer coat with virus directly contacting the lumen wall surface. Stent implantation may be accompanied by anticoagulation therapy as needed.

Example 1 demonstrates the feasibility of the device by demonstrating that significant amounts of virus were retrieved from virus/fibrin mixtures. Example 2 provides a method for loading a fibrin covered stent by liquid wicking of the virus onto the stent. This example demonstrates the ability of significant amounts of virus to be retrieved from fibrin covered stents over time. Example 3 provides a method for introducing the stent into a test animal to test for expression of nucleic acid delivered by the virus in the lumen wall tissues.

In another embodiment of the stents of this invention, a second polymer composition is added over the first polymer composition following, or at the time of virus loading. Preferably the second polymer composition is biodegradable and the second polymer composition coats at least a portion of the lumen-wall contacting surface containing the first polymer composition and virus. For example, after the virus is loaded onto a stent having a first polymer composition coated thereon, the stent can be sprayed with a coating of a biodegradable polymer such as polylactic acid with or without heparin, or another coagulation inhibitory or anti-inflammatory compound. Advantageously, the second covering of polymer provides even greater sustained release capabilities and prevents loss of virus from the coated or covered stent during transit through the body to the target site on the body lumen.

Preferred compositions for the second polymer composition include, but are not limited to fibrin, polylactic acid, polyglycolic acid, polycarbonate and the like or combinations of these compounds.

Virus can be released through a washing action of the stent with body fluids. Virus can also be lost by erosion of the coated surfaces of the stent by dissolution of fibrin or hydrolysis resulting in cross-link cleavage and concomitant release of the physically entrapped virus. The virus can also be released from the first coating or covering composition or from the second polymer composition by diffusion alone or in combination with release of the virus through bioabsorption of the first or second polymer composition. This invention reduces loss of virus from a stent during transit and provides sustained release of virus from the stent when positioned against a lumen wall.

In another example of this invention, the polymer covered stent can be immersed in a solution of methylcellulose. Vacuum can be used to pull the solution into the pores of the first polymer coated stent if desired. Following the methylcellulose coating, the stent is warmed (preferably to about 37° C.) to induce the formation of a methylcellulose-containing gel. This second, biodegradable coating serves to further slow virus erosion and washing from the stent. To coat the lumen-wall contacting surface of the stent with methylcellulose, the stent framework can be positioned over a mandrel cooled to about 4° C. prior to warming the outer surface of the stent framework. The heat differential causes the methylcellulose to preferentially form a gel on the outer surface of the stent.

One or more surfaces of the stent can be coated with one or more additional coats of a polymer that is the same or different from the second polymer coat. For example, alone or in addition to the second polymer coating on the lumen-wall contacting surface of the stent, it is possible to provide another polymer coating or covering composition to the lumen-exposed surface of the stent Preferably the lumen-exposed surface is coated with a negatively charged polymer or biopolymer such as a mucopolysaccharide, an acrylic acid, dextran-sulfate, fucan, fucoidan, polyinosinic acid, heparin, or the like, to minimize diffusion of DNA into the lumen. In one embodiment, a liquid coating is sprayed onto the lumen-exposed surface of the stent either at the time of manufacture or prior to implantation of the device, for example, following virus loading and just prior to the time of implantation. The polymer coating on the lumen-exposed surface is used to prevent virus release from the lumen-exposed surface of the stent when the stent is positioned in the body. This embodiment is particularly useful where the stent is used in the blood vasculature and in particular where the stent is used in the coronary artery.

Figure 3:
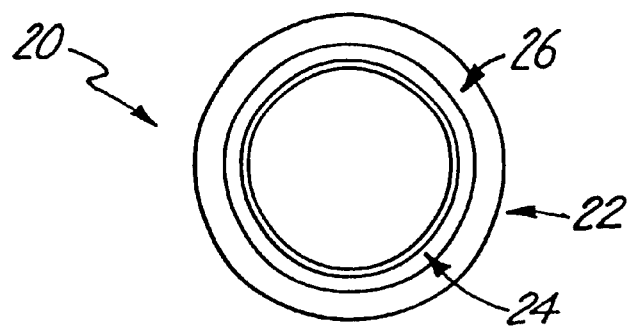
FIG. 3 is a cross-sectional view of a preferred virus-containing fibrin-coated stent according to the present invention.

FIG. 3 provides a cross sectional view of a stent 20 having a first polymer composition comprising fibrin 22 and another polymer covering, preferably a negatively-charged coating, 24 positioned on the lumen-exposed surface of the stent. A stent framework 26 is interposed between the two polymer coverings.

The stents of this invention can be provided in a sterile, dehydrated form, in a hydrated form with virus (shipped frozen or on ice) or as a first polymer covered stent supplied with the necessary materials to facilitate virus loading and further coating or covering of the stent as needed. Therefore, this invention also relates to a kit comprising a stent with a first polymer composition comprising fibrin, buffers suitable for rehydrating the stent and loading the virus and a container to facilitate sterile loading of the stent. Optionally, the kit can include further coatings or coverings to be applied over the first polymer composition on the lumen-wall contacting surface or for covering the lumen-exposed surface of the stent.

There are a number of other variations also contemplated in this invention. For example, it is possible to incorporate drugs and other compounds at the time of virus loading or after virus loading on the polymer covered stent. U.S. Pat. No. 5,510,077 to Dinh et al. discloses the incorporation of drugs into fibrin-covered stents and U.S. Pat. No. 5,464,650 to Berg et al. discloses methods for making stents that include applying a solution of a solvent, a dissolved polymer and a drug to the body of a stent. The drug can be loaded at the time of virus loading, before virus loading or as a step following virus loading. In one embodiment of this invention the drug cyclosporin is loaded with the virus onto the stent to minimize the immune response to adenoviral proteins. The combination of recombinant adenovirus with cyclosporin to minimize the adenoviral-associated immune response is discussed by Nabel (*Circulation* 91(2):541–548, 1995). In the present invention, cyclosporin could be added to the polymer covered stent with the virus or as a spray, following virus loading with, for example, a second polymer coat, such as a spray of polylactic acid.

For certain applications, it can be possible to inactivate the virus capable of delivering nucleic acid to a cell by binding the DNA that has been condensed with polylysine (for example, see *Proc. Natl. Acad. Sci. (USA)* 89:6094–6098, 1992). The inactivated virus is then coupled to transferrin and incorporated into the polymer covered stent either by saturation through liquid wicking or through the application of the virus by spray. The transferrin ligand binds to the transferrin receptor on the cell and is incorporated into the cell using receptor-mediated delivery of the virus transferrin complex. The inactivated virus disrupts the lysosomes in the host cell, reducing DNA degradation and releasing DNA into the cytoplasm.

All references and publications cited herein are expressly incorporated by reference into this disclosure. Particular embodiments of this invention will be discussed in detail and reference has been made to possible variations within the scope of this invention. There are a variety of alternative techniques and procedures available to those of skill in the art which would similarly permit one to successfully perform the intended invention.

EXAMPLE 1

Virus Recovery from Fibrin

To determine whether or not fibrin and polymeric films, such as fibrin, would release virus over time, fibrinogen was mixed with virus, clotted and exposed in liquid to quantitate virus release. Alternatively fibrin films were spiked with virus and exposed to liquid to quantitate virus release.

Fibrinogen (0.76 mL of 26 mg/mL stock clottable fibrinogen in Tris buffer, pH 7.4) was mixed with 0.1 mL of A-MuLV (Amphotropic Murine Leukemia Virus, American Type Culture Collection (ATCC), Rockville, Md.) virus stock and thrombin (0.14 mL of 8 $\mu$g/mL, Parke-Davis). The total volume of the mixture was 1.0 mL. The reagents were combined and allowed to clot for 2 hours at 25° C. The clot was placed in 200 mL of sterile water and incubated overnight at 2–8° C. After incubation, a 0.5 mL aliquot was removed, diluted 10-fold with EMEM (Eagles minimum essential medium, Life Technologies, Gaithersburg, Md.), filtered (0.45 $\mu$m), divided into two aliquots and frozen at −70° C. The clot was compressed between absorbent paper for 30 min at 2–8° C. and was dried overnight at 2–8° C. Following dehydration, the clot was incubated in 1 mL EMEM for 2 hours at 2–8° C. A 0.5 mL aliquot was removed, diluted 10-fold with EMEM, filtered and frozen. The clot was placed in TPA (tissue plasminogen activator, 1.5 mL of a 5 mg/mL stock, Calbiochem, La Jolla, Calif.) and incubated for three hours at 35–39° C. After three hours, the solution was vortexed to aid in clot dissociation. A 0.5 mL aliquot was removed, diluted 10-fold with EMEM, filtered as described above, divided into two aliquots and frozen at −70° C. The remaining portion was spiked with 1.7 mL of virus stock. Results indicated that the virus spike introduced into the starting material was approximately 7.88 $\log_{10}$ focus forming units (FFU). The dissolved clot in TPA sample contained 6.76 $\log_{10}$ FFU. The results (see Table 1) indicated that a significant amount of infectious virus can be recovered from TPA dissolved fibrin.

These results confirm that the addition of virus to fibrinogen and the subsequent precessing steps that would be required to make a fibrin covered stent did not prevent recovery of infectious virus from the fibrin since the results of these studies indicated that there was, on average, an 86% recovery of infectious virus from the virus loaded fibrin samples. This indicated that fibrin supported virus and was compatible as a delivery vehicle.

TABLE 1

| Sample | Virus Titer (FFU/ml) | Volume (ml) | Dilution Adjustment | Adjusted Total FFU | $Log_{10}$ of Adj. Total FFU |
|---|---|---|---|---|---|
| Stock Virus Control | $7.5 \times 10^7$ | 1 | 1 | $7.5 \times 10^7$ | 7.88 |
| Water Wash | $5.0 \times 10^1$ | 200 | 10 | $1.0 \times 10^5$ | 5.00 |
| EMEM Incubate | $<3.0 \times 10^0$ | 1 | 10 | $<3.0 \times 10^1$ | <1.48 |
| Dissolved Clot in TPA | $3.8 \times 10^5$ | 1.5 | 10 | $5.7 \times 10^6$ | 6.76 |

In another experimental set, 1 mL of HIV (human immunodeficiency virus) or HAV (hepatitis A virus) virus stock was loaded onto preformed fibrin films weighing between 0.210 g and 0.275 g, by absorption of the virus into the film for 14–18 hours at 2° C.–8° C. The volume of liquid that was not absorbed was measured and stored at −70° C. One film was incubated in TPA (5 mL of 12.5 mg/mL) for 5 hours to dissolve the fibrin films at about 35–39° C. Viruses were recovered from the virus-spiked TPA treated fribrin films.

These experiments in total indicated that a range of virus types and a range of virus sizes could be loaded in and recovered from preformed fibrin films and from fibrin clots formed from a solution of virus and fibrinogen.

EXAMPLE 2

Method for Loading Viruses into Fibrin Covered Stents

Sterile, dehydrated fibrin stents, prepared as described in U.S. Pat. No. 5,510,077 to Dinh et al., were placed in 150 μL of sterile EMEM (or other sterile buffered eucaryotic tissue culture media) containing at least about $10^{10}$ pfu/mL of virus (A-MuLV) for about 14 to about 18 hours at about 2° C. to about 8° C. or for 2 hrs at about 37° C. Alternatively, virus was coated onto the stents at room temperature. The virus solution was preferably drawn up into the inner lumen of the stent to displace trapped air. Stents were incubated in the liquid just until the virus solution was absorbed or the stent was saturated. For experimental use, the volume remaining was calculated to determine the total amount of virus that was loaded onto the stent. The stent was treated with TPA (5 mL of 12.5 mg/mL stock) for about 5 hours at about 35 to about 39° C. Results are provided in Table 2 below.

The results indicated that a substantial amount of virus remained on the stent for two weeks. As desired, virus titers were reduced in the stents over time with increasing incubation times. These results indicated that fibrin is useful for supporting sustained delivery of virus.

TABLE 2

| Time | Stent 1 (Infectious Units) | Stent 2 (Infectious Units) |
|---|---|---|
| Day 0 Control/TPA Dissolved* | $5.6 \times 10^5$ | $9.4 \times 10^5$ |
| 2 Hours | $2.2 \times 10^3$ | $1.3 \times 10^4$ |
| 4 Hours | $1.9 \times 10^4$ | $6.9 \times 10^4$ |
| 24 Hours | $2.1 \times 10^4$ | $5.4 \times 10^4$ |
| 3 Days | $1.1 \times 10^4$ | $4.6 \times 10^4$ |
| 7 Days | $1.0 \times 10^4$ | $3.9 \times 10^4$ |
| 14 Days | $7.9 \times 10^3$ | $9.5 \times 10^3$ |
| 14 Days + TPA = Virus Left* | $7.0 \times 10^3$ | $1.9 \times 10^4$ |

*The TPA-treated samples did not dissolve completely; more virus may still be present in the stents.

In a second set of experiments the ability of fibrin film to take up and release recombinant adenoviral vectors was tested when the fibrin film was positioned on a stent. The adenoviral vector contained the lacZ gene under the control of the CMV immediate early promoter. The films were loaded with $2 \times 10^6$ particle forming units (pfu) and maintained at 37° C. Over 14 days, the stents released approximately 50% of the loaded titer with the greatest release from about 1 to about 3 days. The functionality of this virus was confirmed by infecting aortic smooth muscle cells and demonstrating transgene function (assay for β-galactosidase activity). Similar studies were performed with plasmid DNA and fibrin sleeves. In these studies, the sleeves took up 50–70 μl of DNA containing solution and released greater than approximately 50% plasmid release over the first 24 hours without further significant release over the next 7 days. Gel electrophoresis demonstrated that the plasmid DNA was intact and transfection studies showed the plasmid to be functional. Experiments comparing plasmid DNA release from fibrin with virus release from fibrin demonstrated that the fibrin support provided a unique support for sustained virus release. Sustained release of virus from the stent is important for at least two reasons. First, the ability of the fibrin sleeve to support virus suggests that more virus will be delivered to the site of stent implantation, as compared to plasmid DNA or, by analogy, bare oligonucleotide. Second, it suggests that the composition of fibrin with virus provides a unique vehicle for nucleic acid delivery to the walls of a lumen.

EXAMPLE 3

In Vivo Studies to Detect Gene Delivery via Polymer-covered Stent

To determine whether polymer enhanced gene delivery is capable of efficiently delivering genes into injured coronary arteries, the delivery of adenoviral and nonviral vectors is studied. The reporter gene, human placental alkaline phosphatase (hpAP, GenBank accession number M19159), was incorporated into plasmid pCMVhpAP that is capable of expressing the hpAP gene under the control of the Cytomegalovirus (CMV) immediate early enhancer/promoter regulatory region using a bovine growth hormone polyadenylation signal. The adenovirus vector expressing hpAP is ADV-hpAP as disclosed by Z.-Y. Yang and R. D. Simari et al. (*Proc. Natl. Acad. Sci. USA*, 93:7905–7910, 1996). This is an E1 deleted recombinant adenoviral vector that expresses hpAP. The expression of hpAP is determined using standard histochemical staining for alkaline phosphatase activity.

Fibrin sleeves prepared according to Holmes et al. (*J. American College of Cardiology* 24(2):525–531, 1994) are placed onto a balloon expandable stent (Wiktor, Medtronic, Minneapolis, Minn.) prior to vector addition. Recombinant adenovirus is used at titers of about $10^6$ to about $10^{10}$ pfu/ml and plasmid was used at about 100 μg total DNA. The fibrin covered stents are placed in a solution of the virus or plasmid overnight.

About 20 juvenile pigs are divided into treatment groups (plasmid or virus). Two to 3 coronary arteries are used for stent placement in each animal. This results in about 20 to about 30 arteries for each group. Animals undergo surgery of coronary artery balloon overstretch injury and stent placement on Day 1. The animals are sacrificed 48 hours later to assess the extent of gene delivery. Following sacrifice, the injured and stented arterial sections are harvested and the sections fixed in 10% buffered formalin. Animals receive 12 mg/kg IM Ketamine and 8 mg/kg IM xylazine. Arterial access is obtained through a carotid arterial cut down following infiltration of the ventral neck region with 10 ml of 1% xylocaine. The right external carotid artery is exposed and an 8F hemostatic sheath is placed intra-arterially for access. A bolus of heparin, 10,000 U, is given through the sheath. Under fluoroscopic guidance, using an 8F coronary guiding catheter, the coated stents are deployed in the selected coronary artery. Following deployment, the carotid artery is repaired with interrupted sutures in two layers.

Formalin fixed specimens are paraffin embedded and sectioned into slides. Histochemical staining for alkaline phosphatase is performed using the methods of Y. Yang and R. D. Simari et al.

Tissue samples can also be tested for the presence of virus-delivered nucleic acid using PCR. Oligonucleotide pairs suitable for amplification of the delivered nucleic acid (based on the sequence of the delivered nucleic acid) are prepared by known DNA synthesis methods or obtained connmmercially (such as from Midland, Midland Tex., Synthetic Genetics, Inc. San Diego, Calif.). Tissue samples are processed and subjected to polymerase chain reaction amplification using methods well known in the art (See *PCR Strategies*, Innis, et al. supra).

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

What is claimed is:

1. A method for making a stent to deliver nucleic acid to cells accessible from a wall of a body lumen comprising the steps of:

providing a stent comprising a lumen-wall contacting surface, a lumen-exposed surface, and a first polymer composition comprising fibrin covering at least a portion of the lumen-wall contacting surface to form a polymer covered stent;

preparing virus capable of delivering nucleic acid to the walls of a body lumen; and loading the virus on the first polymer composition.

2. The method of claim 1, wherein the loading step comprises dipping the polymer covered stent into a solution or gel comprising the virus.

3. The method of claim 1, wherein the loading step comprises spraying the polymer covered stent with a solution comprising the virus.

4. The method of claim 1, wherein the loading step comprises wicking a solution comprising the virus onto the polymer covered stent.

5. The method of claim 1 wherein the loading step comprises loading the first polymer composition and virus into a mold.

6. The method of claim 1, wherein the first polymer composition of the providing step is a polymer or copolymer that is viscoelastic, tear-resistant, and biocompatible.

7. The method of claim 1, wherein the first polymer composition of the providing step is capable of dehydration and rehydration.

8. The method of claim 1, wherein the first polymer composition of the providing step comprises fibrin and another polymer forming substance selected from the group consisting of fibrin, alginate, collagen, hyaluronic acid, porous polyurethane, and cellulose.

9. The method of claim 1, wherein the virus of the preparing step is an adenovirus.

10. The method of claim 1, wherein the virus of the preparing step is a retrovirus.

11. The method of claim 1, wherein the nucleic acid of the preparing step directs the expression of a protein in a cell.

12. The method of claim 1, wherein the nucleic acid of the preparing step binds to nucleic acid within a cell.

13. The method of claim 1, wherein the nucleic acid of the preparing step is RNA.

14. The method of claim 1, wherein the nucleic acid of the preparing step is DNA.

15. The method of claim 1, wherein the virus is added just prior to stent implantation.

16. The method of claim 1, wherein the method further comprises the step of covering at least a portion of the lumen-exposed surface with a second polymer composition.

17. The method of claim 16, wherein the covering step is performed before the loading step.

18. The method of claim 14, wherein the covering step is performed after the loading step.

19. The method of claim 1, wherein the method further comprises applying a biodegradable polymer composition to at least a portion of the lumen-wall contacting surface following the loading step.

20. A virus delivery composition comprising:
   a polymer composition comprising fibrin; and
   virus capable of delivering nucleic acid to a cell.

* * * * *